(12) United States Patent
Taeger et al.

(10) Patent No.: US 7,429,614 B2
(45) Date of Patent: Sep. 30, 2008

(54) MEDICAMENT CONTAINING AN EFFECTOR OF THE GLUTATHIONE METABOLISM TOGETHER WITH α-LIPOIC ACID FOR TREATING DIABETES MELLITUS

(75) Inventors: Michael Taeger, Heinrichsberg (DE); Siegfried Ansorge, Hohenwarthe (DE); Gerhard Fries, Wahlitz (DE); Dieter Koegst, Wahlitz (DE)

(73) Assignees: Esparma GmbH, Osterweddigen (DE); IMTM GmbH, Magedeburg (DE)

( * ) Notice: Subject to any disclaimer, the term of this patent is extended or adjusted under 35 U.S.C. 154(b) by 0 days.

(21) Appl. No.: 10/478,174

(22) PCT Filed: May 27, 2002

(86) PCT No.: PCT/EP02/05811

§ 371 (c)(1),
(2), (4) Date: Nov. 18, 2003

(87) PCT Pub. No.: WO02/096398

PCT Pub. Date: Dec. 5, 2002

(65) Prior Publication Data

US 2004/0138311 A1    Jul. 15, 2004

(30) Foreign Application Priority Data

May 28, 2001   (DE) ............................ 101 25 882

(51) Int. Cl.
*A61K 31/385*   (2006.01)
*C07D 339/02*   (2006.01)
(52) U.S. Cl. .............................. 514/440; 549/39

(58) Field of Classification Search ............... 514/440; 549/39
See application file for complete search history.

(56) References Cited

FOREIGN PATENT DOCUMENTS

| DE | 44 20 102 A1 | 12/1995 |
|----|---|---|
| DE | 198 06 354 A1 | 8/1999 |

OTHER PUBLICATIONS

Gillissen et al., Respiratory Med. (1998), vol. 92, pp. 609-623.*
Derick et al., Biochem. Biophy. Research Comm. (1995), vol. 207, No. 1, pp. 258-264.*
Jablonka et al., Archivum Veterinarium Polonicum (1992), vol. 32 (1-2), p. 57-66.*
Biewenga et al., Gen. Pharmac (1997), vol. 29, No. 3, p. 315-331.*
Kahler, Kuklinski, et al.; Diabetes mellitus; Innere Medizin, pp. 223-232; May 1993.
Borcea, Nourooz-Zadeh, et al; Lipoic Acid Decreases Oxidative Stress Even in Diabetic Patients . . . ; Free Radical Biology & Medicine, vol. 22, Nos. 11/12, pp. 1495-1500; 1999.
Hofmann, Schiekofer, et al.; Peripheral blood mononuclear cells isolated from patients with diabetic nephropathy . . . ; Diabetologia, pp. 222-232; Spring 1999.
Jablonka, Ledwozyw, et al.; The influence of Ambroxol on peroxidative processes . . . ; Archivum Veterinarium Polonicum 32; pp. 57-66; 1992.

* cited by examiner

*Primary Examiner*—Taofiq A Solola
(74) *Attorney, Agent, or Firm*—Marshall & Melhorn, LLC

(57) ABSTRACT

The invention relates to a medicament containing an effector of the glutathione metabolism together with α-lipoic acid for treating diabetes mellitus. This medicament enables disturbances of the thiol-disulfide status or those that occur, for example, in diabetes mellitus to be treated simultaneously, separately or in a temporally graduated manner.

7 Claims, 4 Drawing Sheets

MEDICAMENT CONTAINING AN EFFECTOR OF THE GLUTATHIONE METABOLISM TOGETHER WITH α-LIPOIC ACID FOR TREATING DIABETES MELLITUS

BACKGROUND OF THE INVENTION

This invention relates to the use of the combination of α-lipoic acid and effectors of the glutathione metabolism for the treatment of disruptions of the cellular thiol status and related illnesses.

The precise regulation of the thiol disulfide status represents one of the most important basic requirements of biological metabolisms. The central regulating element within this system is the tripeptide glutathione, which reaches high intracellular concentrations (up to 10 mM) in reduced form. In addition to glutathione, protein groups carrying thiol groups intracellularly and particularly in cell-membrane-bonded form are additional important components of the thiol disulfide status of each cell.

The metabolism of the breakup of disulfide and the formation of the thiol groups, which is regulated by various classes of enzymes, is essential for any normal cell function as a result of the variety of the biological functions of thiol in, among other things, cell growth and differentiation processes including programmed cell death as well as cell protection and decontamination mechanisms overall. Disruptions in this system and changes in the concentration of thiol lead to serious disruptions in cell function, which remain locally limited only in isolated cases, and generally have an adverse effect on the entire organism.

The involvement of a disrupted thiol disulfide status in acute and chronic diseases has been demonstrated in a number of experiments.

In neurodegenerative diseases such as Parkinson's Disease, for example, significant changes in the thiol metabolism have been demonstrated in certain nerve cells (Brain Res Rev 1997; 25:335-358). There are clear indications that as a result of this metabolic disruption, there is an increased death of nerve cells in the functionally impaired areas of the brain, the basal ganglia, which is primarily responsible for the symptoms of the disease (Ann Neurol 1994; 36:348-355).

Reduced glutathione levels and a reduced intracellular glutathione content have also been found in the context of angiopathies and their consequences—arteriosclerosis and heart attack—in the endothelial cells that line the inner wall of the vessel. (Med Sci Res 1998:26:105-106).

Pulmonary diseases that involve a transformation of the pulmonary tissue are regularly connected with a glutathione deficit in the tissue. In a pulmonary fibrosis of this type, the severity of the disease runs parallel to the thiol loss (Chin Chim Acta 1997; 265:113-119). Serious inflammatory pulmonary diseases, investigated using the example of acute difficulty of breathing in adults, were accompanied by a dysregulation of the thiol metabolism of the participating inflammatory cells (granulocytes) (Chest 1996; 109:163-166).

On the basis of the author's own tests, the immuno-competent defensive cells of the 15 bronchial system (alveolar macrophages) in smokers and in patients with chronic obstructive respiratory diseases exhibit a serious cellular thiol deficit. The severity of the disruption of the cellular thiol status is thereby directly correlated with restrictions in lung function (Free Radic Biol Med 2000; 29:1160-1165).

Extensive research into the significance of the glutathione metabolism in viral infections has revealed both a poorer prognosis of thiol-deficient cells based on a compromised cellular defense, as well as an antiviral function of the glutathione that combats the reproduction of the virus (Proc Natl Acad Sci USA 1997; 94:1967-1972).

The author's own tests have shown that the cellular thiol disulfide metabolism is seriously disrupted, particularly under the conditions of severely restricted kidney function and the resulting necessary renal replacement therapy in the form of hemodialysis or peritoneal dialysis. This disruption results in, among other things, the extensive loss of normal cell functions, such as the phagocytosis capability of peritoneal macrophages or the activation of lymphocytes.

The human cellular immune system, which consists of the white blood cells granulocytes, lymphocytes and monocytes, represents a system that reacts particularly sensitively to a disruption in the thiol metabolism.

Minimal changes, particularly losses of cellular glutathione, can trigger a cascade-like program for the self-destruction of the cells, the programmed cell death (apoptosis) (FASEB J 1998; 12:479-486). In this case, the thiol disulfide metabolism acts as a central switching mechanism of an intact immune system, without which the organism would not be viable.

In recent years, moreover, there have been increasing references to a damaged thiol metabolism in chronic kidney diseases (Ren Fail 1998; 20:1 17-124), anemias (Br J Haematol 1995; 91:811-819), premature newborns (Pediatr Pulmonol 1995; 20:160 166), hearing loss caused by noise (Brain Res 1998; 784:82-90), inflammatory bowel diseases (Gut 1998; 42:485-492) and particularly in diabetes mellitus (Metabolism: Clinical and Experimental 1998; 47(8):993-997).

Studies in the context of diabetes mellitus and associated metabolic disruptions have demonstrated both a shift of the redox status at the expense of reduced glutathione as well as an absolute reduction of the total glutathione pool (Free Radic Biol Med 1998; 24:699-704). In the summary of the previous literature on the role of the disruption of the thiol disulfide status, it has been assumed that not only is there an accompanying SH deficit as a consequence of the primary disease, which is Type 1 or Type 2 diabetes, but that a dysregulation in the thiol metabolism is at least one factor that triggers the disease. A convincing example has been provided, among other things, by the verification of the radical-induced destruction of the pancreatic B-cells (Diabet Med 2000; 17:171-180).

It is also known that the disease is accompanied by a number of immunological disruptions. The primary factor that has been identified is an imbalance of the immunoregulator cytokine, which is related to functional disruptions of the lymphocytes and macrophages, with a resulting significant increase in the sensitivity of the patients to infections (Horm Metab Res 1998; 30:526-530).

The correction of a disrupted thiol metabolism thus acquires fundamental importance as a basic therapy in the treatment of a number of diseases of different geneses, particularly, however, under the conditions of diabetes mellitus.

α-lipoic acid has been used relatively successfully in the form of a neuro-protective substance for the treatment of neuro-toxically caused paresthesia in the context of diabetic polyneuropathy (Diabetologica 1995; 38: 1425-1433, Diabetes Res Clin Pract 1995; 29:19-26, Diab Care 1999; 22:1296-1301, Drug Metab Rev 1997; 29:1025-1054, DE 43 43 592 C2). DE 44 47 599 C2 and EP 0 530 446 B1 also describe the use of α-lipoic acid in additional neuronal disruptions, including tinnitus and apoplectiform deafness.

In this case, the cytoprotective mechanism of action depends on the influence of the sugar-dependent protein modification (protein glycolysis), on a reduction of neuro-toxic ketogenesis, and finally on the anti-oxidation function of the α-lipoic acid and its metabolites (Free Radic Biol Med 1995; 19:227-250).

This cell protection function has been investigated particularly from the point of view of the prevention of the oxidative transformation of essentially unsaturated fatty acids. Such an inhibition of the lipid peroxidation, in addition to the use of the α-lipoic acid as a neuro-protection agent, represents the basis for an application as a medicament to protect the liver in the treatment of various intoxications and liver diseases (Biochemistry 1998; 37:1357-1364).

It has also been shown that α-lipoic acid inhibits the reproduction of the HIV virus in different stages of its growth and may thus counteract a progression of the AIDS disease. The results of these laboratory tests can be applied to clinical studies only to a limited extent, however (FEBS-Lett 1996; 394:9-13). The same is true for the detection of an anti-inflammatory function of the substance for the insulin-producing islet cells of the pancreas (Agents Actions 1993; 38:60-65).

EP 0 812 590 A2 and EP 0 427 247 B1 disclose the use of α-lipoic acid as a cyto-protective, as an analgesic and as a medicament for the treatment of inflammatory diseases.

The anti-oxidative properties of α-lipoic acid are based on its ability to form chelates with metal ions and to eliminate radicals directly, as well as on its function as a strong reducing agent. To perform this reaction on an intracellular level, α-lipoic acid, even in reduced form, must be present in the form of dihydrolipoic acid. The transition from (disulfide) α-lipoic acid by means of reduction into the dithiol form of dihydrolipoic acid for its part consumes reducing equivalents, whereby this process is catalyzed by, among other things, the enzyme glutathione reductase (Gen Pharmacol 1997; 29:315-331). This process is apparently the cause of the unsatisfactory action of the substance in terms of thiol restitution.

Ambroxol, i.e. trans-4-(2-amino-3,5-dibromobenzylamino)-cyclohexane hydrochloride, is administered in various forms as an expectorant in the treatment of pulmonary and bronchial diseases (WO 96 33704, GB 2239242, WO 01 05378). Its use in the treatment of hyperuricemia is also known from DE 35 30 761. The action of ambroxol as a mucolytic is based both on a stimulation of surfactant production by the bronchial cells and particularly on its ability to eliminate free radicals (Respir Med 1998; 92:609-23). The anti-oxidative activity of the substance based on these properties was demonstrated primarily on pulmonary cells (Pharmacol 1999; 59:135-141), but also in the context of inflammatory mechanisms (Inflamm Res 1999; 48:86-93). It is also known that through the use of ambroxol in high doses, enzymes that regulate the glutathione metabolism can be influenced directly and peroxidative processes can be inhibited in vitro (Arch Vet Pol 1992; 32:57-66).

SUMMARY OF THE INVENTION

The object of the present invention was therefore to make available novel medicaments containing thiol-reactive substances for the improved stabilization of an impaired thiol disulfide status in the treatment of diabetes mellitus and for the restitution of the functional losses caused by said disease.

The invention teaches that this object can be achieved by a medicament containing ambroxol having the Formula I,

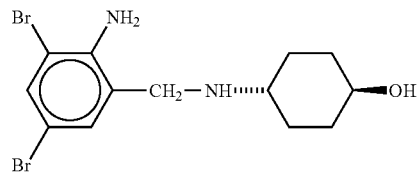

Its salts and/or prodrugs, together with α-lipoic acid, its salts and/or prodrugs as combination preparation for the simultaneous, separate or temporally graduated treatment of a disturbance of the thiol-disulfide status in diabetes mellitus and clinical pictures in which a disruption of the thiol-disulfide status of immune cells occurs. Additional optional feature are also described herein below, as are some of possible uses of the medicament.

According to the invention, effectors of the glutathione metabolism are used in combination with α-lipoic acid, its salts and/or its prodrugs.

DESCRIPTION OF THE PREFERRED EMBODIMENTS

Figure 1:
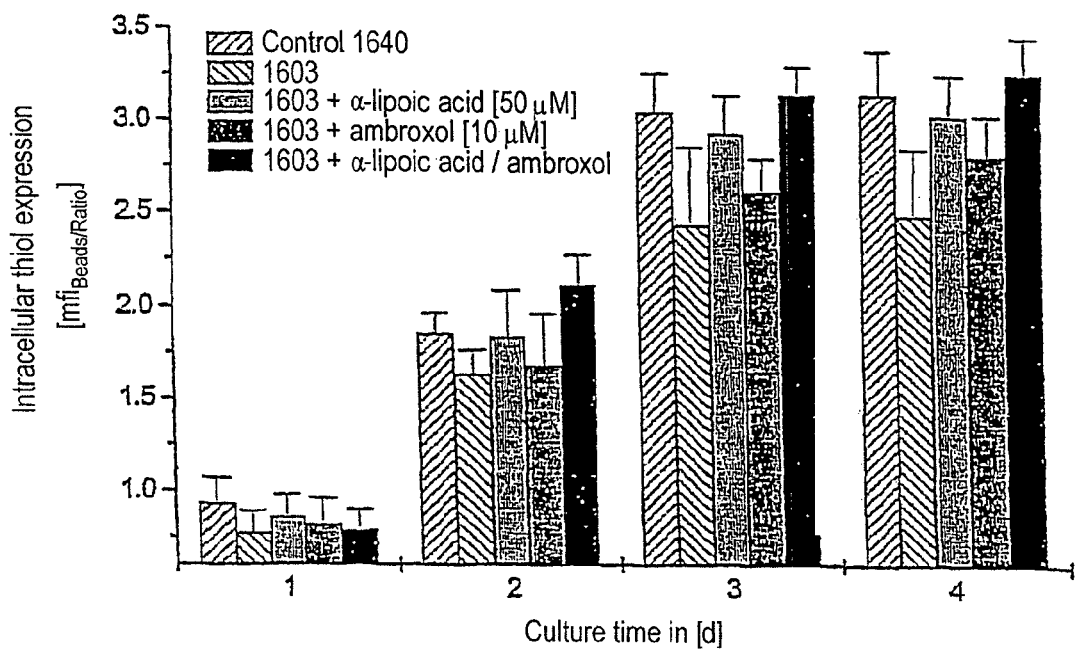
FIG. 1 is a chart illustrating the effect of the combination of α-lipoic acid and ambroxol on the intracellular thiol expression of lymphocytes.

The invention teaches that as a result of the application of the combination of α-lipoic acid and an effector of the glutathione metabolism used according to the invention, there is a normalization of the primary reduced thiol status of immune cells. Not only does the thiol-stabilizing action of the combinations regularly exceed that of the use of α-lipoic acid or of the respective effectors individually, but super-additive effects have also been found. The restitution of the thiol status thereby comprises both intra-cellular thiols as well as membrane-bonded SH groups and is thus an expression of a complex biological regulation. This phenomenon is based on the fact that the effectors of the glutathione metabolism on the one hand eliminate intermediary free radicals that occur, and on the other hand increase the availability of reducing equivalents for the transformation of the α-lipoic acid from disulfide into reduced form, and thus enhance the synthesis-inducing effect of the α-lipoic acid on the thiol disulfide status.

It also became clear that a thiol-increasing effect of the combination of effectors of the glutathione metabolism and α-lipoic acid occurred only in primarily thiol-deficient immune cells. Healthy immune cells, which do not have any alteration of the thiol disulfide status, did not react with a further increase of the SH concentration.

The restitution of the thiol status of the immune cells was accompanied by a normalization of functional parameters. This phenomenon related in particular to the immuno-modulatory effects in the context of the activation of T-lymphocytes.

It has also been demonstrated that the combinations used according to the invention stabilize the thiol disulfide status of additional immune cells such as the peritoneal macrophages of patients who required dialysis. The peritoneal macrophages from high-glucose peritoneal dialysis fluids, prior to treatment with α-lipoic acid/ambroxol in addition to a deficient thiol status, have an almost complete loss of their phagocytosis function, as well as a serious disruption of differentiation and cytokine synthesis, which have been described as causes of the high infection rates in these patients. These functional losses were eliminated by the addition of the combinations according to the invention.

This medicament is particularly appropriate for the treatment of diabetes mellitus as well as other clinical pictures in which there is a disruption of the thiol disulfide status of the immune cells. The treatment can therefore be administered simultaneously, in separate formulations, or in a temporally graduated manner.

The combination preparations used according to the invention can be administered in the conventional pharmacological forms of administration or in the form of an instillate, as well as prophylactically and therapeutically. The effective dose must thereby be determined on a case-by-case basis. The dose for applications in human patients is preferably between 30 and 1200 mg/d, with particular preference given to doses between 200 and 600 mg/d.

In one variant, ambroxol having the general formula I

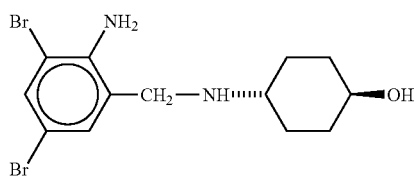

its salt and/or its prodrug are used as the effector of the glutathione metabolism. The dose of ambroxol for applications in human medicine is therefore preferably between 7.5 and 90 mg/d, with particular preference given to doses between 60 and 75 mg/d.

The medicament can thereby he administered orally and/or parenterally.

The medicament can also contain the conventional additives. Such additives include, for example, aqueous solvents, stabilizers, suspension agents, dispersion agents and wetting agents.

The medicament can be manufactured in any desired formulation. By way of example, acceptable formulations include solutions, granulates, powder, emulsions, tablets and/or coated tablets.

According to the invention, an effector of the glutathione metabolism together with α-lipoic acid, its salt and/or its prodrugs, are used for the manufacture of a medicament for the treatment of a disruption of the thiol disulfide status of immune cells in the treatment of diabetes mellitus.

Likewise, an effector of the glutathione metabolism together with α-lipoic acid, its salt and/or its prodrugs can be used for the manufacture of a medicament for a treatment to modulate immunity, increase defenses or inhibit inflammation.

The components of the combination preparation can therefore be in a single formulation or in separate formulations.

The use of the combination of α-lipoic acid and effects of the glutathione metabolism according to the invention is described in greater detail below with reference to examples and the accompanying figures.

Example 1

Influence on the Cellular Thiol Status of Human Peripheral Immune Cells

Peripheral immune cells from healthy donors (n=9) were isolated from the peripheral blood. The major fraction of the resulting total population of mononuclear cells regularly represents lymphocytes with a relative percentage of approximately 90%, depending on the donor. 10% of the mononuclear cells are represented by monocytes.

The mononuclear cells obtained were absorbed in special cell culture media and 25 incubated in a gasifying incubation cabinet at 37° C., a relative humidity of 98% and 5% relative air-$CO_2$ content. The metabolism of the primarily inactive immune cells was activated by means of mitogenic stimulation (0.5 μg/ml phytohemagglutinin). To test the influence of the combinations used according to the invention on the thiol status of thiol-deficient immune cells, these cells were artificially thiol-depleted. This process was carried out using proven methods by cultivation in thiol-deficient media (RPMI 1603). Comparative cultures using complete media (RPMI) 1640 were used to define the best possible normal value under the culture conditions.

The determination of the intercellular thiol content on the single-cell level was made using 5-chloromethyliluorescein diacetate (CMFDA) in flow cytofluorimetry.

Primarily non-fluorogenic CMIFDA is thereby passively absorbed by the cell. By means of the chlormethyl group, there is a bonding to cytoplasmic thiol groups. After the breakdown of the acetate groups by non-specific cellular esterases, this complex, which is now cell membrane bound, becomes fluorogenic at an excitation wavelength $\lambda_{ex}$=490 nm with an emission wavelength $\lambda_{em}$=520 nm. The median fluorescence intensity of the specimen (10,000 cells) is directly proportional to the concentration of the intracellular thiol groups.

The expression of membrane-bound thiol groups was also determined using flow cytofluorimetry. In this case, chloromethyltetramethyl rhodamine (CMTMR) was used as thiol conjugate under the conditions of a blocked membrane potential and an inhibited diffusion capacity of the cells. The fluorescence intensity of the fluorochrome molecules bound to the cell membrane is in turn proportional to the number of thiol groups on the cell surface.

FIG. 1 illustrates the effect of the combination of α-lipoic acid and ambroxol on the intracellular thiol expression of lymphocytes. The data are presented as the ratio of the cellular fluorescence intensity to the respective calibration particles (beads) that were analyzed simultaneously. The actives concentration of the respective combination is identical to the concentrations of the individual components.

Peripheral immune cells were cultivated over a period of 4 days under standard (Control 1640) or thiol-deficient conditions (1603) for the induction of a 10-20% thiol reduction. As illustrated in 1, the addition of ambroxol in combination with α-lipoic acid beginning after 48 hours of treatment resulted in a total compensation of the intracellular thiol deficit. It was not possible to achieve a complete compensation of the thiol deficit using either α-lipoic acid alone or with the individual application of the effector.

Figure 2:
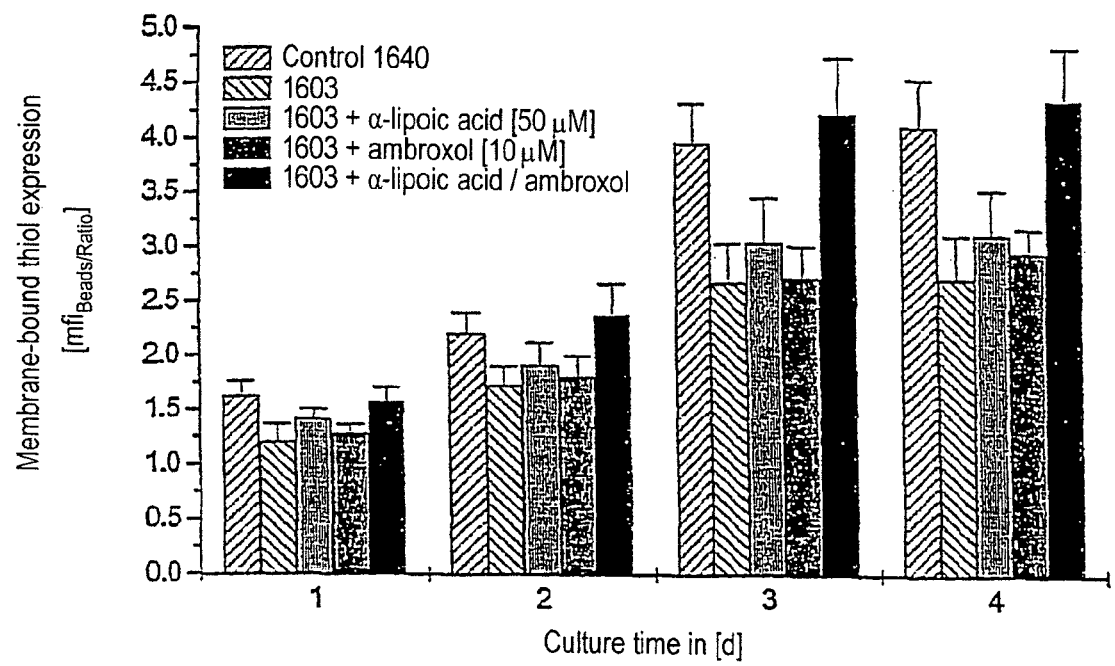
FIG. 2 is a chart illustrating the effect of the combination of α-lipoic acid and ambroxol on the expression of lymphocytes of cell membrane bound thiols.

The results obtained with this experimental investigation of the influence of the combinations according to the invention on the expression of cell membrane bound thiols are presented in FIG. 2 for the combinations of α-lipoic acid and ambroxol. In the treatment using the combination of α-lipoic acid and ambroxol, there was once again, beginning after 48 hours, a significant improvement in the membrane-bound thiol expression. In this case, it was particularly noteworthy that the addition of the individual substances did not at any time have a significant effect

Example 2

Figure 3:
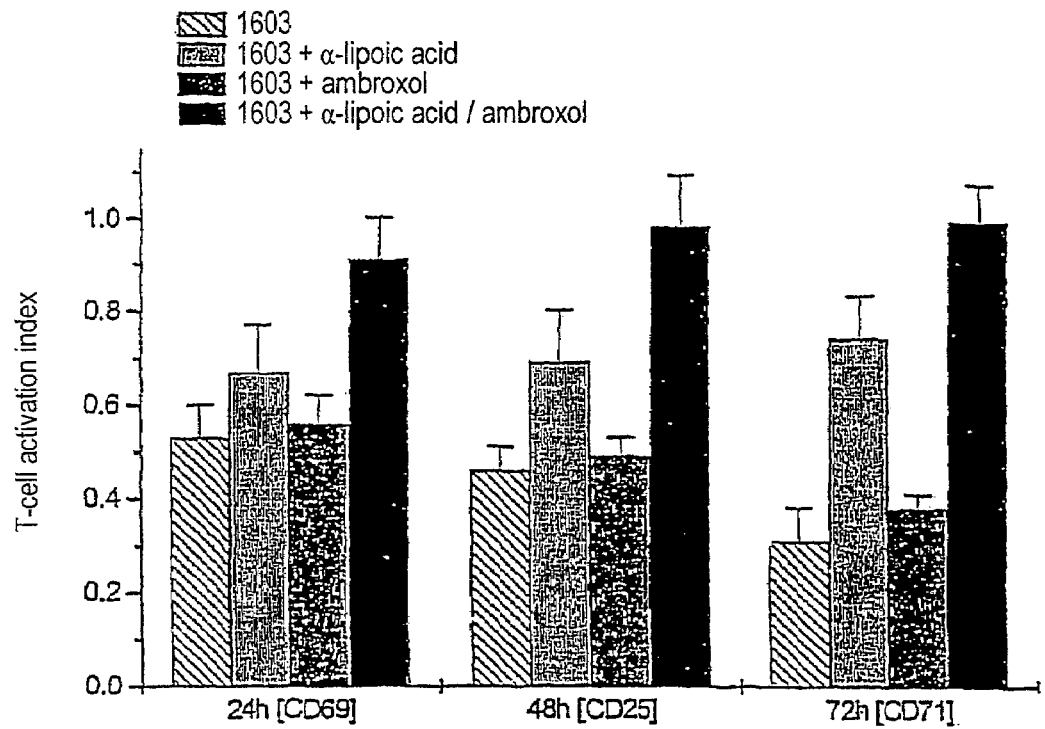
FIG. 3 is a chart illustrating the effect of the combination of α-lipoic acid and ambroxol on the cellular activation status of T-cell lymphocytes.

Influence on the Cellular Activation Status of Human Peripheral T-Lymphocytes In the cultivation experiment described with reference to Example 1, human T-lymphocytes were stimulated with 1.0 μg/ml phytohemagglutinin. In a culture time of 72 hours, specific markers of the cellular activation were quantitatively detected using cytofluorimetery by means of monoclonal antibodies. The influence of the combinations used according to the invention on the activation markers CD69 (early activation antigen), CD25 (intermediate activation antigen) and CD71 (late activation antigen) of T-lymphocytes was measured. FIG. 3 shows the effect of the combination of α-lipoic acid and ambroxol on the activation index of T-lymphocytes. Compared with normal T-lymphocytes (activation index=1.0), in thiol-deficient cells there is a clear reduction of the activation, which demonstrates the disruption of cellular function. After the addition of α-lipoic acid, the well-known effect of a slight improvement of the cellular activation occurs, which however in no case caused any significant difference from the normal control group. Ambroxol does not have any influence on one of the three activation markers. On the other hand, with the combined use of both α-lipoic acid and ambroxol, there was a detectable increase in the T-cell activation index in the normal range. This effect was observed with early, intermediate and hate activation markers. It can thus be concluded that the normalization of the cellular thiol status achieved by the combined use of α-lipoic acid and the respective effector of the glutathione metabolism is accompanied by a restitution of cell function.

Example 3

Influence on the Cellular Thiol Status of Peritoneal Macrophages in the Context of Renal Replacement Therapy Peritoneal macrophages were isolated from the effluate of peritoneal dialysis of patients with a high degree of renal insufficiency, absorbed in a cell culture medium and incubated in a gasifying incubation cabinet at 37° C., a relative humidity of 98% and 7.5% relative air-$CO_2$ content. To investigate the influence of the combinations used according to the invention on the thiol status of the peritoneal macrophages, individual fractions were treated with α-lipoic acid, the effectors of the glutathione metabolism ambroxol and with the combination of α-lipoic acid/ambroxol, while an additional fraction was maintained as an untreated control.

The cellular thiol status was determined using the measurement methods described in Example 1.

Figure 4:
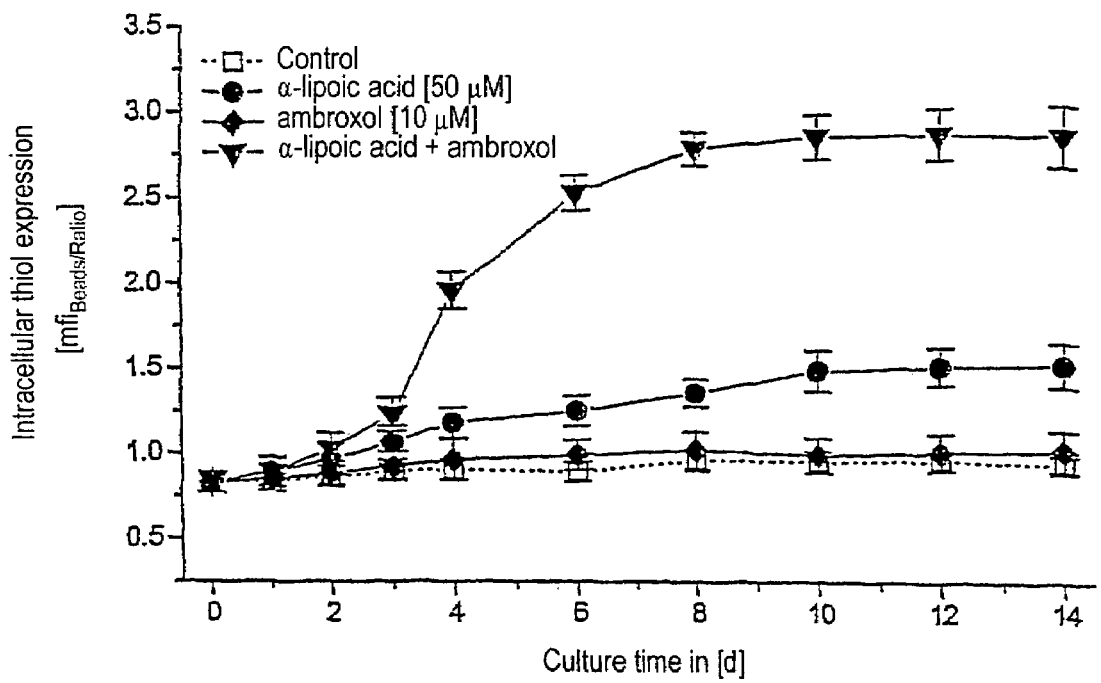
FIG. 4 is a chart illustrating the effect of the combination of α-lipoic acid and ambroxol in a time kinetic over 14 days.

FIG. 4 illustrates the effect of the combination of α-lipoic acid and ambroxolin a time kinetic over 14 days (n=12).

When the individual substances were added, there was again an increase of the cellular thiol expression only when α-lipoic acid was used, while ambroxol had no effect. On the other hand, with the combination of α-lipoic acid and ambroxol, beginning after 72 hours, there was a significant increase of cellular thiol expression, which achieved a super-additive effect after 4 days of treatment and a maximum after 8 days, which exceeded the initial or control data by a factor of three (FIG. 4).

Figure 5:
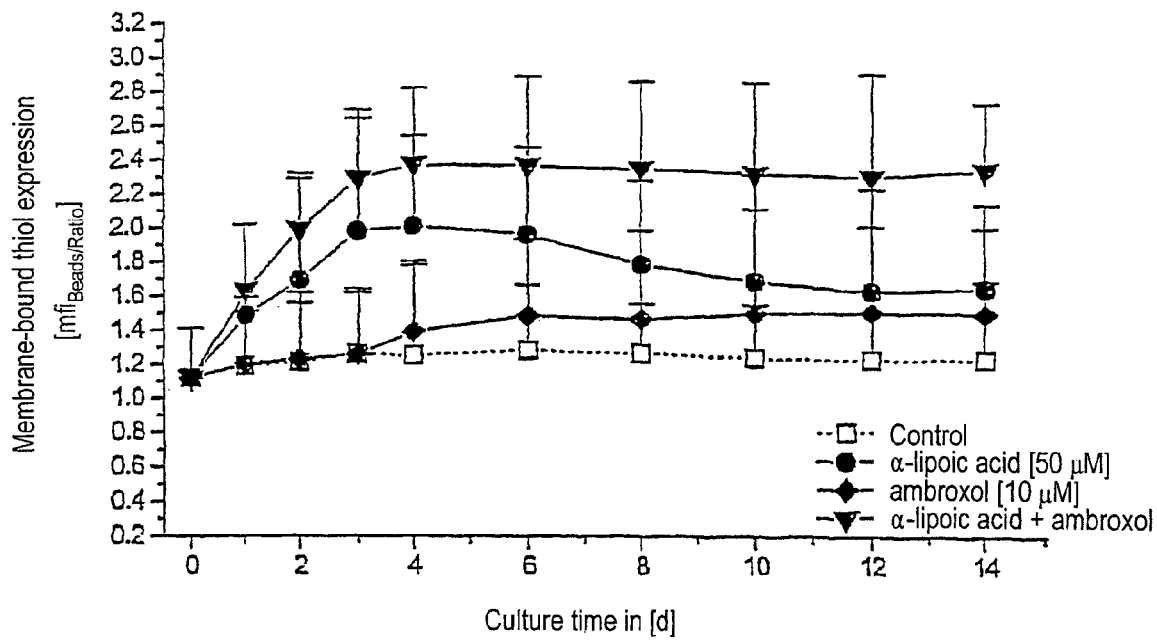
FIG. 5 is a chart illustrating the effect of the combination of α-lipoic acid and ambroxol on the membrane-resistant thiol expression of peritoneal macrophages.

FIG. 5 shows the effect of the combination of α-lipoic acid and enalapril (FIG. 5b) on the membrane-resistant thiol expression of peritoneal macrophages in the experimental system described above. The membrane expression of thiols was determined on the basis of the median fluorescence intensity (mfi) of the specimen (3000 cells/measurement) after coupling to a chlormethyl-fluorochrome derivative.

In comparison with the results of the intracellular thiol expression, in this case there is a very clear effect of the addition of α-lipoic acid by itself, although that effect disappeared after 4 days of treatment. In contrast, the combined application of α-lipoic acid and ambroxol resulted in both a primarily more significant super-additive increase of the membrane-bound thiol expression, and one that was more stable over the observation period.

Example 4

Influence on the Phagocytosis Capacity of Peritoneal Macrophages

Phagocytosis capacity was selected as a measurement to make it possible to characterize the peritoneal macrophages with regard to their original functions.

Peritoneal macrophages were isolated using a method analogous to the method described in Example 3 and cultivated ex vivo.

The phagocytosis capacity was determined by a cytofluorimetric test on the single-cell level. The macrophages were thereby co-cultivated with opsonized and fluorochrome-marked bacteria. The number of bacteria absorbed during a defined period was determined quantitatively by means of the fluorescence intensity in the macrophages and was used as a measurement for their phagocytosis capacity.

The influence of the combinations used according to the invention on the phagocytosis capacity of the peritoneal macrophages after a treatment time of 6 days is presented in the following table.

|  | Phagocytosis rate (mfi / 10,000 cells) |
| --- | --- |
| Control | 371 ± 39 |
| α-lipoic acid [50 μM] | 687 ± 59 |
| Ambroxol [10 μM] | 501 ± 52 |
| α-lipoic acid + ambroxol | 1,398 ± 286 ($p < 0.05$) |

After incubation with α-lipoic acid, ambroxol, the phagocytosis rate was higher than that of the untreated control by a factor of 1.85 (α-lipoic acid), 1.35 (ambroxol). On the other hand, when the combination of α-lipoic acid and ambroxol was used, there was an increase in the phagocytosis rate by a factor of 3.7.

Moreover, a direct correlation was established between the phagocytosis rate and the intracellular thiol content of the peritoneal macrophages for the combination of α-lipoic acid and ambroxol (r=0.79; p<0.01).

Example 5

Influence on the Degree of Differentiation and Activation and the Cytokine Synthesis of Peritoneal Macrophages Peritoneal macrophages were isolated from patients during renal replacement therapy using the method described in Example 3 and cultivated in the presence of the combinations of α-lipoic acid and effector of the glutathione metabolism according to the invention. After 6 days of incubation, the degree of differentiation of the peritoneal macrophages was determined by means of the expression of the cell surface antigens CD15 and CD11c, and the degree of cellular activation was determined using cytofluorimetry by means of the co-expression of the activation antigens CD69 to CD15-positive cells and CD71 to CD11c-positive cells.

The results are presented in the following table:

|  | CD15 | CD11c | CD15/69 | CD11c/71 |
|---|---|---|---|---|
| Control | 1.0 | 1.0 | 1.0 | 1.0 |
| α-lipoic acid [50 µM] | 1.18 ± 0.16 | 1.21 ± 0.11 | 1.09 ± 0.08 | 1.08 ± 0.09 |
| Ambroxol [10 µM] | 0.98 ± 0.13 | 1.01 ± 0.09 | 0.09 ± 0.11 | 0.96 ± 0.1 |
| α-lipoic acid + ambroxol | 1.29 ± 0.21 | 1.65 ± 0.21 | 1.49 ± 0.13 | 1.83 ± 0.14 |

It was shown that the expression of the maturation markers CD15 and CD11c increased markedly with the use of the combination of α-lipoic acid and ambroxol. There was also a significant increase in the activation antigens CD69 and CD71 respectively in the respective cell populations. The application of the single substances had no effect or only a marginal effect on the degree of differentiation and activation of peritoneal macrophages.

Simultaneously, in this experimental approach the cell culture residue was collected and the cytokines Interleukin-6 (IL-6) and Interleukin-1 receptor antagonist (IL-1ra) synthesized and secreted by the peritoneal macrophages contained in the residue were determined. The analysis was performed using the enzyme immunoassay technique with standardized measurement systems.

There was a significant reduction of the IL-6 synthesis in the presence of the combination of α-lipoic acid and ambroxol. This effect in turn went significantly beyond the sum of the reduction achieved by the individual substances. The synthesis of IL-1ra under these conditions was significantly induced. In this case, too, there was a super-additive effect of the combination of α-lipoic acid and ambroxol.

Example 6

Figure 6:
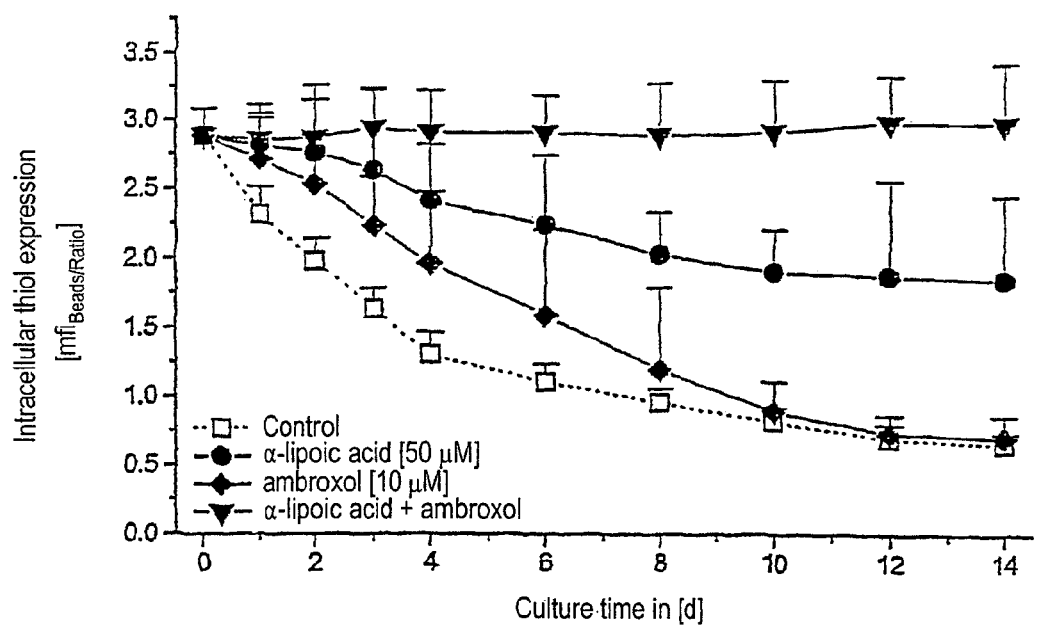
FIG. 6 is a chart illustrating the effect of the combination of α-lipoic acid and ambroxol on the intracellular thiol expression of the peritoneal macrophages in time kinetics.

Influence on the Stability of Thiol Restitution in Peritoneal Macrophages in the Dialysis Model The combinations of thiol-restored peritoneal macrophages used according to the invention were extracted from this test system after 6 days and cultivated over a period of 14 days in a dialysis model. For this purpose the peritoneal macrophages were adapted to matrices that were coated with collagen IV and placed in contact with conventional high-glucose dialysis solution 3 times a day for 60 minutes each time. In this case, the model was used for the induction of a combined hyperglycemic/osmotic stress. FIG. 6 shows the effect of the combination of α-lipoic acid and ambroxol on the intracellular thiol expression of the peritoneal macrophages in time kinetics. The membrane expression of thiol was determined on the basis of the median fluorescence intensity (mfi) of the specimen (3000 cells/measurement) after coupling to a chlormethyl-fluorochrome derivative. While with the primarily thiol-restored controls that had not been treated in this dialysis model, there was a practically linear reduction of the intracellular thiol concentration within the first 4 days, the combined addition of α-lipoic acid and ambroxol resulted in a constant intracellular thiol status on the level of the primary restitution. Here, too, there is a mono-effect of α-lipoic acid, although it lasts only briefly and after approximately 4 days in the dialysis model is only approximately 50% as effective as the combinations.

Figure 7:
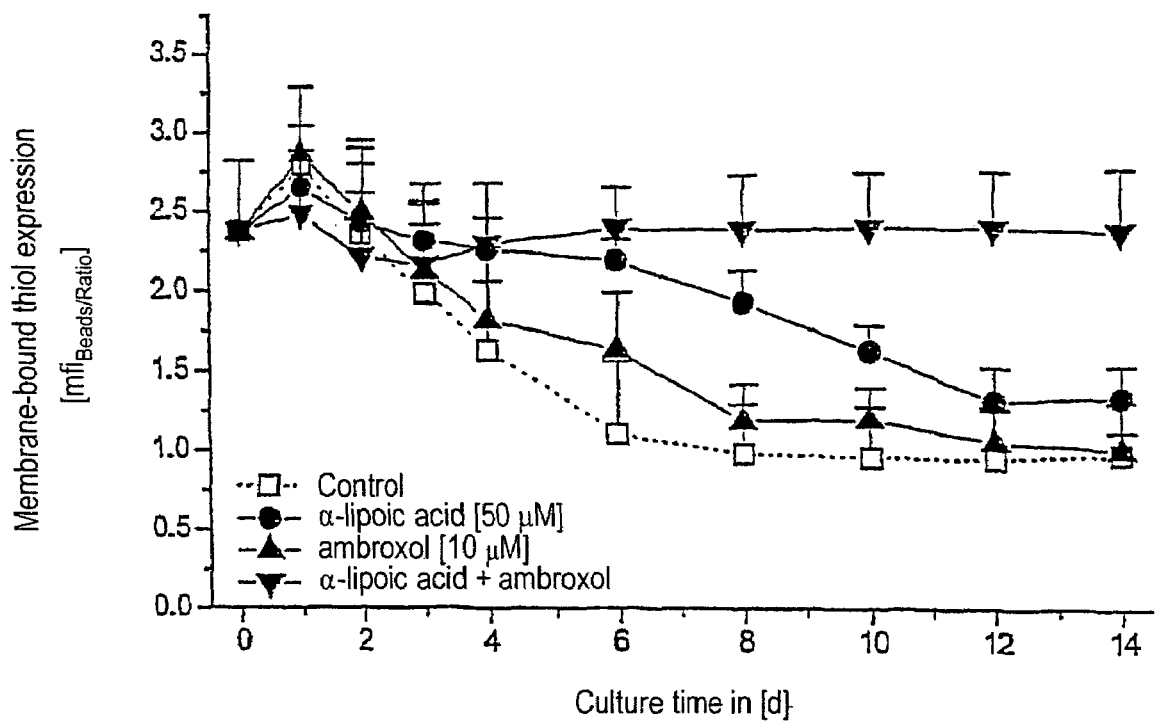
FIG. 7 is a chart illustrating the effect of the combination of α-lipoic acid and ambroxol in the membrane-bound thiol expression.

A similar result is apparent in the curves of the membrane-bound thiol expression illustrated in FIG. 7. Here again, the quantities obtained by the primary thiol restitution are kept constant by the use of the combination of α-lipoic acid and ambroxol, while with the addition of the individual substances, only intermediary (α-lipoic acid) or marginal effects (ambroxol) were observed.

The effects of α-lipoic acid and effector of the cellular glutathione metabolism on the cytokine synthesis of peritoneal macrophages after a treatment of 6 days (n=10) are presented in the following table.

|  | IL-6 [ng/$10^6$ cells] | IL-1ra [ng/$10^6$ cells] |
|---|---|---|
| Control | 53.1 ± 8.9 | 115.2 ± 23.4 |
| α-lipoic acid [50 µM] | 46.9 ± 6.7 | 119.8 ± 19.5 |
| Ambroxol [10 µM] | 51.8 ± 8.1 | 118.6 ± 21.3 |
| α-lipoic acid + ambroxol | 31.5 ± 9.2 (p < 0.05) | 126.8 ± 15.3 (p < 0.05) |

Overall, these tests make it plain that the application of the combination of α-lipoic acid and the effectors of the glutathione metabolism ambroxol stabilizes a primarily massively damaged thiol status in different cell systems. As a result of this normalization, there is also a re-establishment of central cellular immuno-regulatory functions, which is not achieved without such a treatment.

What is claimed is:

1. A method for the treatment of a known symptom of diabetes mellitus, namely a disturbance of the membrane-bound thiol disulfide status in peripheral immune cells, comprising the step of administering a compound selected from the group consisting of ambroxol having the Formula I,

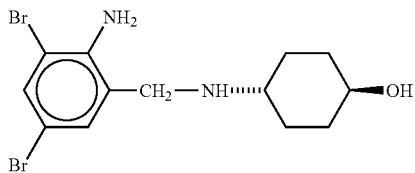

its salts and mixtures thereof in a dosage range of 7.5 mg/d and 90 mg/d, between 60 mg/d and 75 mg/d, and a compound selected from the group consisting of α-lipoic acid, its salts and mixtures thereof in a dosage range of 30 mg/d and 1200 mg/d, or between 200 mg/d and 600 mg/d.

2. A method for the treatment of a known symptom of diabetes mellitus, namely a disturbance of the intracellular thiol disulfide status in peripheral immune cells, comprising the step of administering a compound selected from the group consisting of ambroxol having the Formula I,

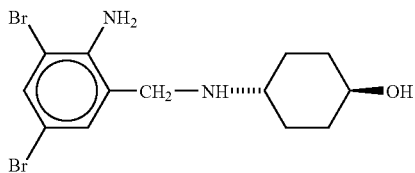

its salts and mixtures thereof in a dosage range of 7.5 mg/d and 90 mg/d, between 60 mg/d and 75 mg/d, and a compound selected from the group consisting of α-lipoic acid, its salts and mixtures thereof in a dosage range of 30 mg/d and 1200 mg/d, or between 200 mg/d and 600 mg/d.

3. A method for treatment of a disturbance of the thiol disulfide status according to any of claims 1-2, where the cells described are peripheral immune cells of patients with diabetes mellitus.

4. A method for the activation of thiol-deficient T-cells, including the step of administering a compound selected from the group consisting of ambroxol having the Formula I,

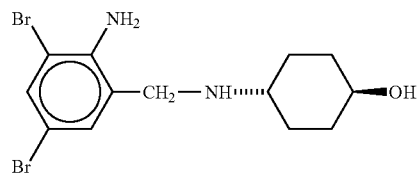

its salts and mixtures thereof in a dosage range of 7.5 mg/d and 90 mg/d, between 60 mg/d and 75 mg/d, and a compound selected from the group consisting of α-lipoic acid, its salts and mixtures thereof in a dosage range of 30 mg/d and 1200 mg/d, or between 200 mg/d and 600 mg/d.

5. Method of treatment as recited in any one of claims 1, 2, 4, wherein the medicament is administered orally or parenterally.

6. Method of treatment as recited in any one of claims 1, 2, 4, wherein the medicament contains additional additives selected from the group consisting of aqueous solvents, stabilizers, suspension, dispersion and wetting agents.

7. Method of treatment as recited in any one of claims 1, 2, 4, wherein the medicament is in the form of a solution, a granulate, a powder, an emulsion, a tablet and/or coated tablet.

* * * * *